United States Patent [19]

Soriano et al.

[11] Patent Number: 4,507,251
[45] Date of Patent: Mar. 26, 1985

[54] β-OXIMINOALKYLPHOSPHONIC ACID ESTERS

[75] Inventors: David S. Soriano, Cheektowaga; Timothy R. Demmin, Grand Island; Martin A. Robinson, East Amherst, all of N.Y.

[73] Assignee: Allied Corporation, Morris Township, Morris County, N.J.

[21] Appl. No.: 401,792

[22] Filed: Jul. 26, 1982

Related U.S. Application Data

[63] Continuation-in-part of Ser. No. 339,269, Jan. 15, 1982, abandoned.

[51] Int. Cl.$^3$ .......................... C07F 9/40; A01N 57/12
[52] U.S. Cl. ................. 260/944; 260/927 R; 260/969; 71/86
[58] Field of Search ........................... 260/944, 927 R

[56] References Cited

U.S. PATENT DOCUMENTS 3,819,751  6/1974  Dixon .................................. 260/944

OTHER PUBLICATIONS

Gryszkiewicz-Trochimowski et al., "Chem. Abstracts" vol. 65, 18610h, (1966).
"A Novel Route to α-Aminoalkylphosphonic Acids and Dialkyl α-Aminoalkylphosphonate Hydrochlorides", K. D. Berlin, et al., J. Am. Chem. Soc., 90, 4494 (1968).
"Fast, Neighbouring Group-Induced Rearrangement During Alkaline Hydrolysis of α-Hydroxyimino-p-Nitrobenzyl Phosphates, Phosphonates, and Phosphinates", J. I. G. Cadogan, et al., J. Chem. Soc. Perkin II, 1798 (1973).
"Preparation of Oxoalkanephosphonic Acids", J. Zygmunt, et al., Synthesis, 609 (1978).
"Preparation and Properties of Phosphorus-Containing Oximes", E. E. Borisova, et al., Zh. Obshch. Kim., 48, 767 (1978); CA, 89, 43626 (1978).
"Participation of a Neighbouring Oxime Group in Phosphonate Ester Hydrolysis", C. N. Lieske, et al., Chem. Commun., 13, (1968).
"Structure, Reactivity, and Biological Activity of O-(Diethyl Phosphoryl)Oximes and O-(Methylcarbamoyl)Oximes of Substituted Acetophenones and α-Substituted Benzaldehydes", T. R. Fukuto, et al., J. Agr. Food Chem., 17, 923 (1969).
"Nucleophilic Addition and Subsequent Oxime-Assisted Ester Hydrolysis of Diethyl β-Ketopropylphosphonate", P. Livant, et al., J. Org. Chem. 43, 3011 (1978).
"Reaction of Trimethylphosphite with Acetone Oxime", M. P. Osipova, et al., CA, 93, 220863 (1980).
"Reactions of Silyl Phosphites with α-Halo Carbonyl Compounds, Elucidation of the Mechanism of the Perkow Reaction and Related Reactions with Confirmed Experiments", M. Sekine, et al., J. Org. Chem., 46, 2097 (1981).

*Primary Examiner*—Anton H. Sutto
*Attorney, Agent, or Firm*—Richard C. Stewart, II

[57] ABSTRACT

Novel β-oximinoalkylphosphonic acid ester derivatives of general formula B are prepared from the corresponding α-halo oxime A:

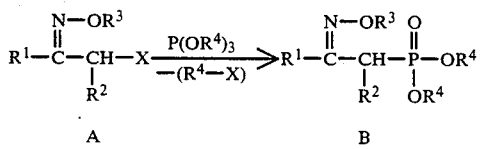

wherein
$R^1$ is a substituent selected from the group consisting of H and $C_1$–$C_{20}$ alkyl, cycloalkyl and aryl substituents;
$R^2$ is a substituent selected from the group consisting of H and $C_1$ to $C_{20}$ linear alkyl and aryl substituents;
$R^3$ is a substituent selected from the group consisting of H and $C_1$ to $C_{20}$ alkyl, cycloalkyl, 1-alkoxy alkyl, aryl, acyl, N-substituted carbamoyl, N,N-disubstituted carbamoyl and nitrogen-, oxygen-, sulfur-, and phosphorus-containing heterocyclic substituents;
$R^4$ is an alkyl substituent of $C_1$ to $C_{20}$ aryl; and
X is a substituent selected from the group consisting of Cl, Br, I.

In a specific reaction, the α-halo oxime derivative is dissolved in an excess of trialkyl phosphite, greater than 3 molar equivalents is preferred. The preference for the α-halogen atom follows the order I>>Br>>Cl which parallels their rate of reaction with trialkyl phosphite. The acceptable temperature range includes ambient conditions. The reaction can be run in various solvents including tetrahydrofuran, toluene and acetonitrile. The reaction time is generally in excess of one hour and usually 4–18 hours. The reaction mixture does not require special precautions to protect from oxygen or atmospheric moisture. When the reaction is complete the product may be separated by vacuum distillation, recrystallization or column chromatography. An alternate isolation procedure involves dissolving the reaction mixture in a suitable solvent, e.g., methylene chloride, washing soluble by-products, drying and evaporating the solvent followed by vacuum distillation, recrystallization or column chromatography.

9 Claims, No Drawings

β-OXIMINOALKYLPHOSPHONIC ACID ESTERS

BACKGROUND OF THE INVENTION

This is a continuation-in-part application of U.S. patent application Ser. No. 339,269 filed on Jan. 15, 1982, now abandoned.

FIELD OF THE INVENTION

This invention relates to phosphonic acid ester derivatives and more particularly to a novel class of phosphonic acid derivatives containing a β-oximinoalkyl functional group. These β-oximinoalkylphosphonic acid ester derivatives are useful in the areas of agriculture and hydrometallurgy.

DESCRIPTION OF THE PRIOR ART

The reaction of alkyl halides, R'—X, with trialkyl phosphites, P(OR)$_3$, at elevated temperature to provide alkyl phosphonic acid esters,

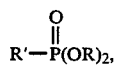

and alkyl halide, R—X, is known as the Arbuzov reaction which is referred to hereinbelow. However, α-haloketones under standard Arbuzov conditions normally yield a mixture of products including the expected β-ketoalkylphosphonate ester plus an enol phosphate generated by another pathway called the Perkow reaction also referred to hereinbelow. There is only one known report, that of P. Livant and M. Cocivera, J. Org. Chemistry, 43, 3011 (1978) on the oximation of β-ketophosphonates. The oximinophosphonate referred to in that report was not isolated and was characterized only by its H-nmr spectrum.

Another alkylphosphonate synthesis involves reacting a salt of dialkyl phosphite with an organohalide. This procedure, known as the Michaelis-Arbuzov reaction, (Ref. citation) has not been applied to α-halo oximes.

When oximes are treated with trialkyl phosphite at elevated temperature both oxime O-alkylation and phosphorus attack at the imino carbon occur to give an α-(alkoxyamino)alkylphosphonic acid ester as described by M. P. Osipova, et al., Calif. 93;220863 (1980). We are aware of no prior knowledge of reactions of simple oximes with trialkyl phosphite at room temperature. The prior art referred to above as well as other known related work are summarized in the eight reactions which follow (1) The reaction of α-Haloketone+Trialkyl Phosphite

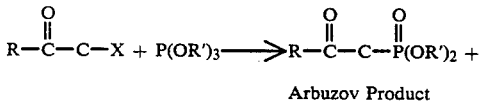

Arbuzov Product

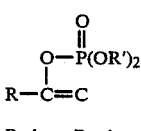

Perkow Product described by M. Sekine, K. Okimoto, K. Yamada and T. Hata, J. Org. Chem., 46, 2097 (1981).

(2) The reaction of Oxime+Trialkyl Phosphite

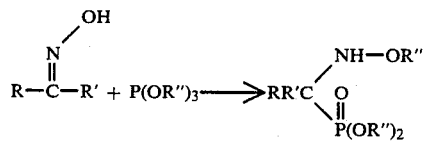

described by M. P. Osipova, et al., Calif. 93: 220863.

(3) The reaction of Nitroalkene and Trialkyl Phosphite

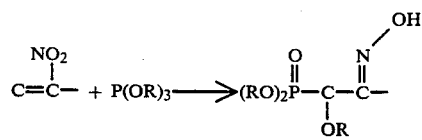

described by E. Borisova, N. Vafina, T. Zyablikova, A. Il'Yasova, E. Trutneva, and I. Shermergorn, Zh. Obshch. Khim., 48, 767 (1978), Calif. 89:43626.

(4) The reaction of α-Halo Oxime and Phosphonic Acid Salt

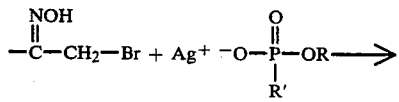

(β-Oximinoalkyl Ester
of a Phosphonic Acid)

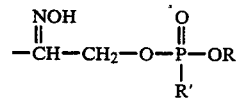

described by C. N. Lieske, Joseph W. Hovanec, George M. Steinberg, and P. Blumbergh, Chem. Commun., 13 (1968).

(5) Oxime+Phosphorochloridate

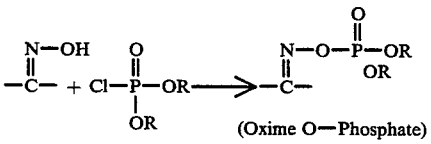

(Oxime O—Phosphate)

T. Fukuto, R. Metcalf, R. Jones, and R. Myers, J. Agr. Food Chem., 17, 923 (1969).

(6) The reaction of Acid Chloride+Trialkylphosphite, followed by Hydroxylamine

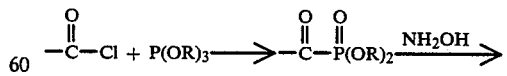

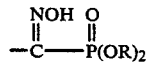

K. Berlin, N. Roy, R. Claunch, and D. Bride, J. Am. Chem. Soc., 90, 4494 (1968).

(7) The reaction of β-Oxoalkylphosphonate+Hydroxylamine

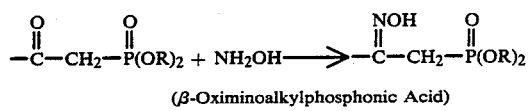

(β-Oximinoalkylphosphonic Acid)

described by P. Livant and M. Cocivera, J. Org. Chem., 43, 3011 (1978).

(8) The reaction of Phosphonic Acid + Nitrile Oxide

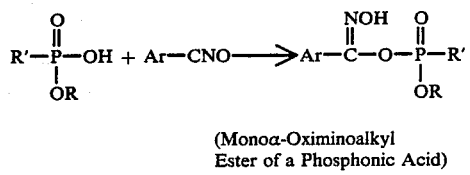

(Monoα-Oximinoalkyl Ester of a Phosphonic Acid)

described by J. Cadogan, D. Eastlick, J. Challis, and A. Cooper, J. Chem. Soc. Perkin II, 1798 (1973).

SUMMARY OF THE INVENTION

In accordance with the invention α-bromo or α-iodo oximes react exothermically with trialkylphosphites at room temperature to give β-oximinoalkylphosphonic acid esters. Analogous oxime O-ethers, -carbamates, and -esters may be similarly used. α-Chloro oximes also may be rapidly converted into the desired phosphonate esters under mild conditions by a modified procedure involving treatment with a mixture of sodium iodide in trialkyl phosphite (described hereinafter). β-Oximinoalkylphosphonates may also be prepared by an ionic phosphonylation reaction between sodium dialkylphosphite and the α-halooxime (or ketone). The β-oximinoalkylphosphonic acid esters are easily isolated, stable compounds. In nearly all cases the reactions are clean with no evidence of (1) phosphite addition to the imino carbon or (2) Perkow mode of attack on the halo oxime system.

DESCRIPTION OF THE PREFERRED EMBODIMENTS

In accordance with the invention, novel β-oximinoalkylphosphonic ester derivatives of the general formula B may be prepared from the corresponding α-halo oxime of the formula A. However, it will be understood that the corresponding β-oximinoalkylphosphonic acids and salts may also be prepared by one skilled in the art by the hydrolysis of the phosphonate ester derivative using suitable methods such as the procedure described by J. Zygmunt, P. Kafarski, P. Mastalery, Synthesis, 609 (1978).

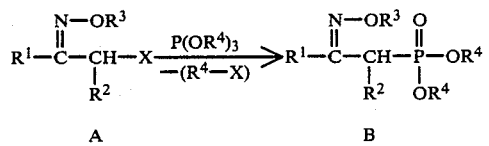

wherein $R^1$ is a substituent selected from the group consisting of H and $C_1$–$C_{20}$ alkyl, cycloalkyl and aryl substituents;

$R^2$ is a substituent selected from the group consisting of H and $C_1$ to $C_{20}$ linear alkyl and aryl substituents;

$R^3$ is a substituent selected from the group consisting of H and $C_1$ to $C_{20}$ alkyl, cycloalkyl, 1-alkoxy alkyl, aryl, acyl, N-substituted carbamoyl, N,N-disubstituted carbamoyl, and nitrogen-, oxygen-, sulfur-, and phosphorus-containing heterocyclic substituents;

$R^4$ is an alkyl substituent of $C_1$ to $C_{20}$; and

X is a substituent selected from the group consisting of Cl, Br, I.

The β-oximinoalkylphosphonic acid esters can be oils or solids and are generally soluble in most organic solvents including toluene, tetrahydrofuran, methanol, and methylene chloride. The lower molecular weight derivatives, e.g. of the formula B wherein $R^1 = R^4 = CH_3$, and $R^2 = R^3 = H$; and $R^1 = t$-$C_4H_9$, $R^2 = H$, $R^3 = COCH^3$ and $R^4 = CH_3$ are appreciably water soluble.

The process for making β-oximinoalkylphosphonic acid esters of the formula B typically involves dissolving an α-bromo oxime (or α-iodo oxime) in an excess of trialkyl phosphite at room temperature (Procedure A of Example 1). The progress of the reaction is monitored by a procedure such as thin layer chromatography, infrared or NMR Spectroscopy. After the appropriate reaction time at room temperature (α-chloro oximes generally react sluggishly or are inert under these conditions) the reaction mixture is evaporated at reduced pressure and the product isolated by distillation, recrystallization, liquid chromatography, or column chromatography. Alternatively, the reaction mixture can be diluted with methylene chloride (or another suitable organic solvent) and washed with water thoroughly to remove excess phosphite. The organic layer is then dried, evaporated and the product isolated as before.

Two other alternate processes, Procedures B and C, are described in Examples 2 and 3, respectively.

A fourth process, Procedure D of Example 4, provides a certain refinement on the Procedures A, B, and C, since by this method even α-chloro derivatives are converted to the oximinophosphonate. Procedure D involves treating the α-chloro or α-bromo oxime (or ketone) with a mixture of sodium iodide (1 molar equivalent) partially dissolved in trialkyl phosphite (excess). Potassium iodide may also be employed. Apparently a rapid iodide-halide exchange occurs and the α-iodo oxime (or ketone) generated in situ reacts quickly and cleanly with the phosphite to form the desired phosphonated oxime (or ketone). The α-iodo oximes (or ketones) have previously been prepared in a separate step by the classical Finkelstein reaction (iodide-halide exchange) and are preferred starting materials because of their selective, rapid reactivity towards trialkyl phosphite. In the reaction of the halogenated ketones, under these conditions the percent of Perkow side reaction is believed to be greatly diminished when compared with the standard Arbuzov reaction. Also, this method for converting α-chloro ketones to the corresponding dialkyphosphonate is more rapid (2–4 hours) and may be conducted at room temperature.

In the preparation of the novel compounds of the invention, the α-halo oxime derivative is dissolved in an excess of trialkyl phosphite, greater than 3 molar equivalents is preferred. The preference of the α-halogen atom follows the order I>>Br>>Cl which parallels their rate of reaction with trialkyl phosphite. The acceptable temperature range for conducting the reaction is 10° C.–100° C.; the preferred range is 15° C.–35° C. The acceptable pressure range is 1–3 atm; the preferred pressure is 1 atm. The reaction can be run in various solvents including tetrahydrofuran, toluene and acetonitrile; the preferred solvent is excess trialkyl phosphite.

The reaction time is generally in excess of one hour and most often in the order of 4–18 hours. The reaction mixture does not require special precautions to protect from oxygen or atmospheric moisture.

Starting materials include any α-haloketone many of which are commercially available or they may be prepared by known methods. Reaction of the α-haloketone with hydroxylamine in aqueous alcohol provides the α-halo oxime. The α-halo oximes can also be synthesized by reacting nitrosyl chloride with any mono, di or trisubstituted olefin at room temperature or below in various solvents, e.g. sulfur dioxide.

The preferred β-oximinoalkylphosphonic acid derivatives of the general formula B in accordance with the invention are those represented by the formula

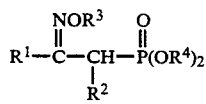

where $R^1 = CH_3$, $t-C_4H_9$, $C_6H_5$; $R^2 = H$ and $R^3 = H$, $CH_3$ $COCH_3$, $CONHCH_3$; and $R^4 = CH_3$. The invention will be described in greater detail by way of the following examples. In the examples, general procedures for preparing β-oximinoalkylphosphonic acid esters are given followed by the results obtained with the representative examples. The results are further summarized in the Table which follows the examples.

EXAMPLE 1

Dimethyl 2-[O-(Acetyl)oximino]-2-phenethylphosphonate

Procedure A—Use of Neat Trialkyl Phosphite

α-Bromoacetophenone oxime 0-acetate (30.0 g, 0.117 mole) was dissolved in trimethyl phosphite (22.1 g, 0.178 mole) with stirring at room temperature. After 18 hours 100 mL of ice water and 100 mL of methylene chloride were added with stirring. The organic layer was separated, dried and evaporated to give the crude product. The side product, dimethyl methylphosphonate, was removed by distillation in vacuo (30°–40° C./0.1 mm) and the oily residue was shown to be 99% pure by NMR and HPLC analysis. 30.7 g (92% yield).

The following spectral data was obtained for the product

NMR* H-NMR (CDCl$_3$)δ 2.25 (S, 3H, Methyl), 3.50 (D, 2H, Methylene, J=24.8 Hz.), 3.65 (D, 6H, Methyl(-POCH$_3$), J=11.25 Hz.), 7.60(M, 5H, Aromatic).
*NMR Spectrum obtained on a 90 MHz. Perkin-Elmer-32 instrument.

| Elemental Analysis | C | H | N | |
|---|---|---|---|---|
| | 53.46 | 6.45 | 4.47 | (Calc.) |
| | 53.20 | 6.70 | 4.40 | (Found) |

HPLC** Spectrum showed one component using a refractive index detector (Flow Rate 2.9 1ml/min, Chart Speed 0.5 cm/min, Solvent 50% AQ. Methanol, Retention Time: 53.3 min.)
**Waters Model 440 using a reverse-phase preparative column.

EXAMPLE 2

Diethyl 2-[O-(N-methylcarbamoyl)oximino]-2-phenethylphosphonate.

Procedure B—Using refluxing Tetrahydrofuran (or Toluene) with 1.1 Molar Equivalents of Trialkyl Phosphite To a solution of α-bromoacetophenone oxime O-(N-methyl)carbamate (3.00 g, 0.013 mole) in dry toluene (40 ml) was added triethyl phosphite (2.32 g, 0.014 mole). The homogeneous solution was heated to reflux until the analysis indicated complete reaction and the volatiles were removed in vacuo to yield the crude solid which was then re-crystallized from petroleum ether, M.P. 77°–78° C., 3.17 g (81% yield).

EXAMPLE 3

Dimethyl 2-[O-(2-methoxy-2-propyl)oximino]-2-phenethylphosphonate

Procedure C—Use of Sodium Dialkyl Phosphite in Tetrahydrofuran

A solution of dimethyl phosphite (3.0 g, 0.027 mole) in dry tetrahydrofuran (20 mL) was added dropwise to a stirred suspension of sodium hydride (1.3 g, 0.027 mole) in tetrahydrofuran (20 mL) at 0° C. When hydrogen gas evolution ceased (approx. 30 min.) the mixture was warmed to room temperature and a solution of α-bromoacetophenone oxime-O-[(2-methoxy)-2-propyl] ether (7.7 g, 0.027 mole) in tetrahydrofuran (20 mL) was added over 20 minutes. The mixture was warmed to 35° for 1 hour and then evaporated in vacuo. The residue was dissolved in methylene chloride (100 mL) and washed with water, then dried with magnesium sulfate (anhyd.). Evaporation to dryness gave 8.1 g (95% yield) of the desired phosphonate as determined by NMR spectroscopy.

EXAMPLE 4

Dimethyl 3,3-Dimethyl-2-[O-(acetyl)oximino]-butylphosphonate

Procedure D—Sodium Iodide in Trimethyl Phosphite

A mixture of α-bromo and α-chloro pinacolone oxime-O-acetate (ca 1:1, 1.00 g, ca 4.6 MMole) was dissolved in trimethyl phosphite (10 mL) at 0° C. Sodium iodide (0.9 g, 6 mmole) was added at once with stirring and the mixture was warmed to 20° C. over 4 hours. Saturated ammonium chloride solution (100 mL) and methylene chloride (100 mL) were added at once. The organic layer was then separated, dried, and evaporated to dryness. The crude product was purified by distilling off the side product dimethyl methylphosphonate (35°–40°/0.1 mm) leaving the desired product, 1.2 g (90% yield) analytically pure as a non-distillable oil.

EXAMPLES 5–22

The results of Examples 5 through 22, following the procedures designated in the Table are summarized in the Table together with those of Examples 1–4.

TABLE I

PREPARATION OF β-OXIMINOALKYLPHOSPHONATES

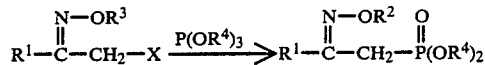

| EX. | PROCEDURE | R¹ | R³ | X | R⁴ | REACTION COND. TIME | BP/MP | ANAL. | YIELD |
|---|---|---|---|---|---|---|---|---|---|
| 1 | A | C₆H₅ | Acetyl | Br | Me | 6–72 hrs | 140–145% IMM | IR, NMR | >90% |
| 2 | B | C₆H₅ | Carbamoyl | Br | Et | 4–5 hrs | 77–78° | (CHN), NMR, IR | 81% |
| 3 | C | C₆H₅ | Ketal | Br | Me | 1–3 hrs 0° 25° | viscous oil | IR, NMR | 95% |
| 4 | D | C₄H₉ | Acetyl | Cl, Br | Me | 4 hrs/25° | viscous oil 112°/.1 MM | NMR, IR, MS | 90% |
| 5 | C | C₆H₅ | Ketal | Cl | Me | 1.5 hrs 0 25° (½ hr steam bath) | viscous oil | IR, NMR | 64% |
| 6 | A | C₆H₅ | Acetyl | Cl | Me | 72 | — | NMR | 0 |
| 7 | A | C₆H₅ | Carbamoyl | Br | Me | 12 hrs | 79–81° | (CHNP), NMR, IR | >90% |
| 8 | A | C₆H₅ | Carbamoyl | Cl | Me | 72 hrs | — | NMR | 0 |
| 9 | B | C₆H₅ | H | Br | Et | 5 hr/D | viscous oil | HRMS, IR, NMR, HPLC | 55% |
| 10 | A | C₆H₅ | H (from Ketal) | Br | Me | 12 hrs | oil | IR, NMR | 65% |
| 11 | A | C₄H₉ | Acetyl | I | Me | 4 hrs | oil 112°/.1 MM | NMR, IR, (CHNP) | >90% |
| 12 | A | C₄H₉ | Carbamoyl | I | Me | 4 hrs | viscous oil | NMR, IR | >90% |
| 13 | A | C₆H₅ | H | Cl | Me | 72 hrs | — | NMR, TLC | >50% |
| 14 | B | C₆H₅ | Acetyl | Br | Et | 12 hrs | 155–160°, 1.1 MM | CHN, NMR, IR | >90% |
| 15 | D | C₄H₉ | Carbamoyl | Cl, Br | Me | 4 hrs/25° | viscous oil | NMR, IR | vis. oil >90% |
| 16 | D | C₄H₉ | NOR³ = O (Ketone) | Br | Me | 4 hrs/25° | oil | NMR, IR, MS | 92% |
| 17 | D | CH₃ | NOR³ = O (Ketone) | Cl | Me | 4 hrs/25° | oil | NMR, IR, MS | Quant. |
| 18 | D | C₆H₅ | NOR³ = O (Ketone) | Cl | Me | 4 hrs/25° | oil | NMR, IR, MS | 70% |
| 19 | D | C₆H₅ | NOR² = O (Ketone) | Br | Me | 4 hrs/25° | oil | NMR, IR, MS | 75% |
| 20 | D | CH₃ | Acetyl | Cl | Me | 4 hrs/25° | viscous oil 115°/1.0 MM | NMR, IR, MS | >90% |
| 21 | D | CH₃ | Carbamoyl | Cl | Me | 50% Complete 1.5 hr/R.T. | oil | NMR, IR | >90% |
| 22 | D | C₄H₉ | H (From Ketal) | Cl, Br | Me | 50% Complete 1.5 hr/R.T. | oil | NMR, IR | >74% |

The β-oximinoalkylphosphonic acids or esters represent a new class of heterosubstituted oxime. These novel structures are useful as nitrification inhibitors (see illustrative test runs provided as Examples 23–27 below) and have applications in various areas including: (1) other agricultural uses, e.g., as plant growth regulants, (2) hydrometallurgy, and (3) as versatile chemical intermediates leading to amides, azirines, aminoketones, etc., each containing phosphonic acid functionality. For example, β-substituted alkylphosphonic acids, e.g., 2-chloroethylphosphonic acid may be used to increase crop yields and accelerate ripening in a variety of fruits and vegetables; some α-substituted oximes are biologically active, e.g., 2-methylthioisobutyraldehyde oxime N-methylcarbamate may be used as a pesticide; some α- and β-substituted phosphonic acids are metal ion complexing agents; and some α- and β-substituted oximes may be used as a transition metal ion complexing agent, e.g., ortho-hydroxybenzophenone oxime derivatives may be used commercially to isolate copper from dilute ore solutions.

EXAMPLES 23–27

In testing the compounds of the invention as nitrification inhibitors, the following procedure was used. A 20μgram sample of the oximinophosphonate compound was added per gram of soil in the presence of 300 ppm of diammonium phosphate as the ammonium (i.e., nitrogen) source. Nitrate production was determined after 10 days by an automatic colorimeter using as a control standard a soil sample containing no oximinophosphonate.

The results are set forth in Table II.

TABLE II

| Example | Compound Name | Structure | Percent of Nitrification Inhibition |
|---|---|---|---|
| 23 | Dimethyl 2-oximinopropane phosphonate | $CH_3-\overset{NOH}{\underset{\|\|}{C}}-CH_2-PO_3Me_2$ | 34% |

TABLE II-continued

| Example | Compound Name | Structure | Percent of Nitrification Inhibition |
|---|---|---|---|
| 24 | Dimethyl 2-[O—(Acetyl)-oximino]-2-phenethan-phophonate | $\phi\text{-}\underset{\underset{\text{NOAc}}{\|}}{C}\text{—}CH_2\text{—}PO_3Me_2$ | 25% |
| 25 | 2-Oximinopropanephosphonic acid monomethyl ester | $CH_3\text{-}\underset{\underset{\text{NOH}}{\|}}{C}\text{—}CH_2\text{—}\underset{\underset{\text{OMe}}{\|}}{\overset{\overset{\text{OH}}{\|}}{P}}O$ | 22% |
| 26 | Dimethyl 2-oxopropane-phosphonate | $CH_3\overset{\overset{O}{\|}}{C}\text{—}CH_2\text{—}PO_3Me_2$ | 43% |
| 27 | Dimethyl 3,3-dimethyl-2-oxobutanephosphonate | $(CH_3)_3C\text{—}\overset{\overset{O}{\|}}{C}\text{—}CH_2PO_3Me_2$ | 36% |

It will be understood that a broad range of products may be prepared within the reactants and ranges disclosed herein and we therefore do not intend to limit the invention except as set forth in the claims which follow.

What we claim is:

1. β-Oximinoalkylphosphonic acid ester derivatives of the general formula:

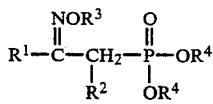

and salts thereof, wherein:

R$^1$ is a substitutent selected from the group consisting of H, C$_1$ to C$_{20}$ alkyl, cycloalkyl, and aryl substituents;

R$^2$ is a substituent selected from the group consisting of H, C$_1$ to C$_{20}$ linear alkyl and aryl substituents;

R$^3$ is a substituent selected from the group consisting of a cycloalkyl, 1-alkoxyalkyl, aryl, acyl, N-substituted carbamoyl and phosphorus containing heterocycle substituents; and R$^4$ is a substituent selected from the group consisting of H and C$_1$ to C$_{20}$ alkyl.

2. The phosphonic acids of the general formula of claim 1, wherein R$^4$ is hydrogen.

3. The salts of the phosphonic acid derivatives of the general formula of claim 1.

4. The ester derivatives of claim 1 wherein R$^1$ and R$^4$ are alkyl substituents.

5. The ester derivative of claim 1, which is dimethyl 2-[O-(acetyl)oximino]-2-phenethylphosphonate.

6. β-Oximinoalkylphosphonic acid ester derivatives of the formula:

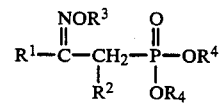

wherein:

R$^1$ is phenyl or 3,3-dimethyl butyl;

R$^2$ is hydrogen;

R$^3$ is N-methylcarbamoyl; and

R$^4$ is methyl or ethyl.

7. The ester derivative of claim 6 which is diethyl 2-[O-(N-methylcarbamoyl)oximino]-2-phenethylphosphonate.

8. The ester derivative of claim 6 which is dimethyl 3,3-dimethyl-2-[O-(N-methylcarbamoyl)oximino]-butylphosphonate.

9. β-Oximinoalkylphosphoric ester derivatives of the general formula:

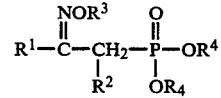

and salts thereof, wherein:

R$^1$ is C$_1$ to about C$_{20}$ alkyl or aryl;

R$^2$ is hydrogen, C$_1$ to about C$_{20}$ alkyl or aryl;

R$^3$ is carbamoyl, N-substituted carbamoyl, N,N-disubstituted carbamoyl, 1-alkoxyalkyl or C$_1$ to about C$_{20}$ alkyl;

R$^4$ is hydrogen or alkyl.

* * * * *